United States Patent [19]

Miller et al.

[11] Patent Number: 5,219,740
[45] Date of Patent: Jun. 15, 1993

[54] RETROVIRAL GENE TRANSFER INTO DIPLOID FIBROBLASTS FOR GENE THERAPY

[75] Inventors: A. Dusty Miller, Seattle; Theo D. Palmer, Bellevue, both of Wash.

[73] Assignee: Fred Hutchinson Cancer Research Center, Seattle, Wash.

[21] Appl. No.: 14,579

[22] Filed: Feb. 13, 1987

[51] Int. Cl.$^5$ .................. C12N 5/10; C12N 15/86
[52] U.S. Cl. .................. 435/69.6; 424/93 A; 424/93 B; 435/172.3; 435/183; 435/193; 435/227; 435/240.1; 435/320.1; 935/32; 935/57; 935/62; 935/70; 935/71
[58] Field of Search .................. 435/68, 172.3, 235, 435/240.1, 172.1, 236, 239, 240.2, 240.21, 320, 948; 424/89, 91, 93, 94, 95, 94.1; 935/6, 22, 32, 34, 57, 60, 62, 63, 66, 70, 71, 79

[56] References Cited

U.S. PATENT DOCUMENTS

| | | | |
|---|---|---|---|
| 4,396,601 | 8/1983 | Salser et al. | 424/94.5 |
| 4,485,096 | 11/1984 | Bell | 424/532 |
| 4,497,796 | 2/1985 | Salser et al. | 514/44 |
| 4,686,098 | 8/1987 | Kopchick et al. | 424/424 |
| 4,861,719 | 8/1989 | Miller | 435/236 |
| 4,868,116 | 9/1989 | Morgan et al. | 435/240.2 |

FOREIGN PATENT DOCUMENTS

| | | |
|---|---|---|
| WO87/00201 | 1/1987 | PCT Int'l Appl. |
| WO89/02468 | 3/1989 | PCT Int'l Appl. |
| WO89/07136 | 8/1989 | PCT Int'l Appl. |

OTHER PUBLICATIONS

D. L. Nelson et al., (1986), Cold Spring Harbor Symp. Quant. Biol., 51(2):1065–1071.
W. W. Kwok et al., (1986), Proc. Natl. Acad. Sci. USA, 83:4552–4555.
S. H. Orkin et al., (1986), Clin. Imm. Immunopath., 40:151–156.
J. G. Hellerman et al., (1984), Proc. Natl. Acad. Sci. USA, 81:5340–5344.
F. D. Ledley et al., (1986), Proc. Natl. Acad. Sci. USA, 83:409–413.
A. D. Miller et al., (1986), Cold Spring Harbor Symp. Quant. Biol., 51(2):1013–1019.
P. A. Wood et al., (1986), Cold Spring Harbor Symp. Quant. Biol., 51(2):1027–1032.
H. E. Gruber et al., (1985), Proc. Natl. Acad. Sci. USA, 82:6662–6666.
P. A. Wood et al., (1986), Somatic Cell and Molecular Genetics, 12(5):493–500.
J. Sorge et al., (1987), Proc. Natl. Acad. Sci. USA, 84:906–909.
H. M. Temin, Retrovirus vectors for gene transfer: Efficient integration into and expression of exogenous DNA in vertebrate cell genomes, in *Gene Transfer*, R. Kucherlapati (Ed.), Plenum Press, N.Y., pp. 149–187, 1986.
A. D. Miller et al., Transfer of genes into somatic cells using retroviral vector, Cold Spring Harbor Symposium, 51, Abstract, Jun. 1986.
Stratowa, C. et al., Recombinant retroviral DNA yielding high expression of hepatitis B surface antigen, *EMBO Journal*, 12(1):1573–1578, 1982.
Cone, R. D., and R. C. Mulligan, High-efficiency gene transfer into mammalian cells: generation of helper-free recombinant retrovirus with broad mammalian host range, *Proc. Natl. Acad. Sci. U.S.A.*, 81:6349–6353, 1984.
*Webster's Ninth New Collegiate Dictionary*, p. 637 ("in vivo"), Merriam-Webster Inc., 1984.

(List continued on next page.)

*Primary Examiner*—Richard A. Schwartz
*Assistant Examiner*—Johnny F. Railey, II
*Attorney, Agent, or Firm*—Christensen, O'Connor, Johnson & Kindness

[57] ABSTRACT

A process of mammalian gene therapy. Explanted fibroblasts are genetically modified by introducing a retroviral construct containing a nucleotide sequence encoding for a therapeutic substance. The genetically modified fibroblasts are implanted into a mammalian subject.

7 Claims, 1 Drawing Sheet

OTHER PUBLICATIONS

Choudary, P. V., et al., Gene transfer of human glucocerebrosidase cDNA to Gaucher fibroblasts: expression of the epitope altered in type 2 phenotype, *DNA*, 5(1):78, Feb. 1986.

Choudary, P. V., et al., Gene transfer and expression of active human glucocerebrosidase in mammalian cell cultures, *DNA*, 5(1):78, Feb. 1986.

Choudary, P. V., et al., Gene transfer by retrovirus and expression of active human glucocerebrosidase, *Fed. Proc.*, 45:1696, May 1986.

Choudary, P. V. et al., Retrovirus-mediated transfer of the human glucocerebrosidase gene to Gaucher fibroblasts, *Mol. Biol. Med.*, 3:293–299, Jun. 1986.

Choudary, P. V. et al., The molecular biology of Gaucher disease and the potential for gene therapy, *Cold Spring Harbor Symposia on Quantitative Biology*, LI:10-47–1052, 1986.

Gazit, A., et al., Mammalian cell transformation by a murine retrovirus vector containing the avian erythroblastosis virus erbB gene, *Journal of Virology*, 60(1):19–28, Oct. 1986.

Demetriou, A. A., Survival, organization and function of microcarrier-attached hepatocytes transplated in rats. *Proc. Natl. Acad. Sci. USA*, 83:7475–7479, Oct. 1986.

Palmer, T., et al., Efficient retrovirus-mediated transfer and expression of a human adenosine deaminase gene in diploid skin fibroblasts from an adenosine deaminase-deficient human, *Proc. Natl. Acad. Sci. USA*, 84:1055–1059, Feb. 1987.

Garver, R. I., et al., Colonal gene therapy: in vivo expression of a transplated monoclonal population of murine fibroblasts containing a retrovirus inserted human $\alpha_1$-antitrypsin gene, *Transactions of the Association of American Physicians*, C:10–20, 1987.

Palmer, T. D., et al., Production of human factor IX in animals by genetically modified skin fibroblasts: potential therapy for hemophilia B, *Blood*, 73(2):438–445, Feb. 1989.

St. Louis, D., and I. M. Verma, An alternative approach to somatic gene therapy, *Proc. Natl. Acad. Sci. USA*, 85:3150–354, May 1988.

Selden, R. F., et al., Implantation of genetically engineered fibroblasts into mice: implications for gene therapy, *Science*, 236:714–718, May 1987.

Garver, R. I., et al., Clonal gene therapy: transplanted mouse fibroblast clones express human $\alpha 1$-antitrypsin gene in vivo, *Science*, 237:762–764, Aug. 1987.

Munnich, A., et al., "Letter to the Editor: Enzyme replacement therapy by transplantation of HLA-compatible fibroblasts in Sanfilippo syndrome: Another trail", Pediatr. Res., 16:259–260, 1982.

Dean, M. F., et al., "Letter to the Editor: Effectiveness of HLA-compatible fibroblasts for enzyme replacement Therapy in the mucopolysaccharidoses", Pediatr. Res., 16:260–261, 1982.

Debenham, P. G., et al., "DNA-mediated gene transfer into human diploid fibroblasts derived from normal and ataxia-telangiectasia donor: Parameters for DNA transfer and properties of DNA transformants", Int. J. Radiat. Biol., 45(5):525–536, 1984.

Yoakum, G. H., et al., "High-frequency transfection and cytopathology of the hepatitis B virus core antigen in human cells", Science, 222:385–389, 1983.

Miller, A. D., et al., "A transmissible retrovirus expressing human hypoxanthine phosphoribosyltransferase (HPRT): Gene transfer into cells obtained from human dificient in HPRT", Proc. Natl. Acad. Sci. USA, 80:4709–4713, 1983.

Hock, R. A., et al., "Retrovirus-mediated transfer and expression of drug resistance gene in human haematopoietic progenitor cells", Nature, 320:275–277, Mar. 20, 1986.

Williams, D. A. et al., "Retrovirus-mediated transfer of human adenosine deaminase gene sequences into cells in culture and into murine hematopoietic cells in vivo", Proc. Natl. Acad. Sci. USA, 83:2566–2570, Apr. 1986.

Valerio, D., et al., "Cloning of human adenosine deaminase cDNA and expression in mouse cells", Gene, 31:147–153, 1984.

Sher, S. E., et al., "Acceptance of allogeneic fibroblasts in skin equivalent transplants", Transplantation, 36(5):552–557, 1983.

Bell, E., et al., "Living tissue formed in vitro and accepted as skin-equivalent tissue of full thickness", Science, 211:1052–1054, 1981.

Miller, A. D., et al., "Factors involved in production of helper virus-free retrovirus vectors", Somatic Cell Molec. Genet., 12(2):175–183, 1986.

Miller, A. D., et al., "Generation of helper-free amphotropic retroviruses that transduce a dominant-acting, methotrexate-resistant dihydrofolate reductase gene", Molec. Cell. Biol., 5(3):431–437, 1985.

Emerman, M., et al., "Genes with promoters in retrovirus vectors can be independently suppressed by an epigenetic mechanism", Cell, 39:459–467, Dec. 1984 (Part 2).

RETROVIRAL GENE TRANSFER INTO DIPLOID FIBROBLASTS FOR GENE THERAPY

This invention was made with Government support under one or more of grants CA41455, CA09351, AG00057, and AI19565 awarded by the National Institutes of Health. The Government has certain rights in this invention.

TECHNICAL FIELD

This invention relates to genetic engineering and, more particularly, to processes and compositions useful for mammalian somatic gene therapy.

BACKGROUND OF THE INVENTION

Fibroblasts have been used previously in an attempt to cure genetic disease. HLA-matched fibroblasts from normal donors were subcutaneously injected into patients suffering from various forms of mucopolysaccharidosis (MPS). Mannich, A., et al., Pediatr. Res. 16: 259–260, 1982; Dean, M. F., et al., Pediatr. Res. 16: 260–261, 1982. Although the normal fibroblasts were able to reverse the accumulation of metabolic intermediates in tissue culture, there were only minor, transient alterations in metabolic products in the patients' serum, and there were no changes in the patients' overall condition. The fibroblasts in these experiments produced only normal levels of enzyme and may have been subject to graft rejection. In addition, it is not known if the pathophysiological effects of the enzyme deficiency in MPS patients are reversible.

Studies on transfer and expression of genes in human fibroblasts have been severely limited by the short in vitro replicative life span of normal human diploid fibroblast cells and by inefficient gene transfer techniques. Debenham, P. G., et al., Int. J. Radiat. Biol. 45: 525–536, 1984; Yoakum, G. H., et al., Science 222: 385–389, 1983.

Retrovirus vectors offer an alternative for gene transfer. Amphotropic murine retroviruses can infect immortalized human fibroblast cells (Miller, A. D., et al., Proc. Natl. Acad. Sci. USA 80: 4709–4713, 1983), but it is not known whether retroviral infection of normal human fibroblasts would be inhibited due to their different growth characteristics. This issue is important since many human genetic diseases such as oncogenic transformation exhibit phenotypes that are masked in immortalized cells.

SUMMARY OF THE INVENTION

The invention provides a process for efficiently introducing genes of therapeutic importance into normal human diploid fibroblasts, so as to permit and facilitate the expression of the introduced gene(s) following implantation of the genetically modified fibroblasts into a mammalian subject. Briefly stated, normal diploid fibroblasts are explanted from a mammalian subject and genetically modified by the introduction of a retroviral construct containing a nucleotide sequence encoding for a therapeutic substance. The genetically modified fibroblasts are implanted into either the autologous donor or into another mammalian subject that is otherwise deficient in the therapeutic substance. Prior to implantation, the treated fibroblasts may be screened for genetically modified fibroblasts containing and expressing the construct. For this purpose, the retroviral construct can also be provided with a second nucleotide sequence encoding an expression product that confers resistance to a selectable marker substance. Suitable selectable markers for screening non-immortalized fibroblasts include the neomycin analog G418 and Hygromycin-B. The fibroblasts are preferably explanted from the skin, or lung, of the donor, which can be a human or mammal of veterinary importance.

The retroviral construct should be a replication-defective virus. To that end, the replication-defective retroviral construct can lack one or more of the gag, pol, and env sequences required for retroviral replication. A representative retroviral construct suitable for this purpose essentially contains at least one viral long terminal repeat and promoter sequence upstream of the nucleotide sequence for the therapeutic substance and at least one viral long terminal repeat and polyadenylation signal downstream of the therapeutic sequence.

The recipient of the genetically modified fibroblasts will typically be deficient in the therapeutic substance, which can be an enzyme, hormone, or a precursor such as a pro-enzyme or pre-proenzyme. Representative of such therapeutic substances are adenosine deaminase, purine nucleoside phosphorylase, and blood clotting factors such as factors VIII and IX. The modified fibroblasts may be implanted by subcutaneous injection, intraperitoneal injection, or intravenous injection.

BRIEF DESCRIPTION OF THE DRAWINGS

Representative retroviral vectors are shown in FIGS. 1 to 5. These vectors contain selectable genes inserted between long terminal repeats (LTR) and viral replication signals. The 3' LTRs and adjacent sequences are from Moloney murine leukemia virus (Mo-MLV). The 5' LTRs and adjacent sequences of vectors LHL, N2, and LNSAL are also from Mo-MLV, whereas those of vectors LSHL and LHL2 are from Moloney murine sarcoma virus (Mo-MUSV). In the FIGURES, arrows indicate promoters; SV40 indicates the early region enhancers and promoter of simian virus 40; $(A)_n$ indicates polyadenylation signals; and SD and SA are splice donors and splice acceptors, respectively; kb, kilobase. The normal splice donor in Mo-MUSV at position 206 was removed by a single base substitution (AGGT to AGGC) in the LHL2 and LSHL vectors. The N2 and LNSAL vectors contain the selectable gene coding for neomycin phosphotransferase (neo). Vectors LHL, LHL2, and LSHL contain the selectable hygromycin phosphotransferase gene (hph). N2, LHL, and LNSAL contain approximately 400 base pairs of the gag coding region of Mo-MLV, while LHL2 and LSHL do not contain this region. The LNSAL vector distinctively contains a gene for expressing adenosine deaminase (ADA), linked to an SV40 early region enhancer-promoter, downstream of the neo gene.

DETAILED DESCRIPTION OF THE PREFERRED EMBODIMENT

Figure 1:
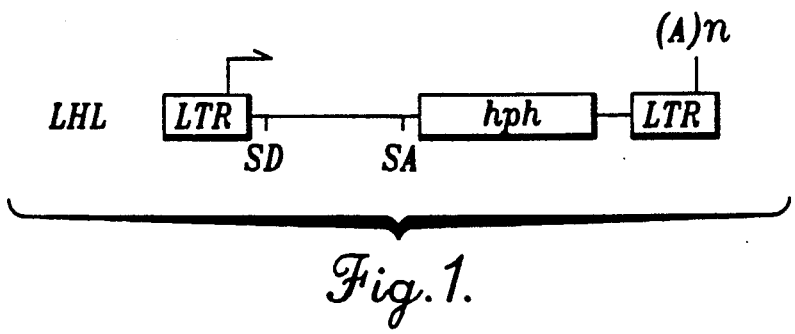
Figure 2:
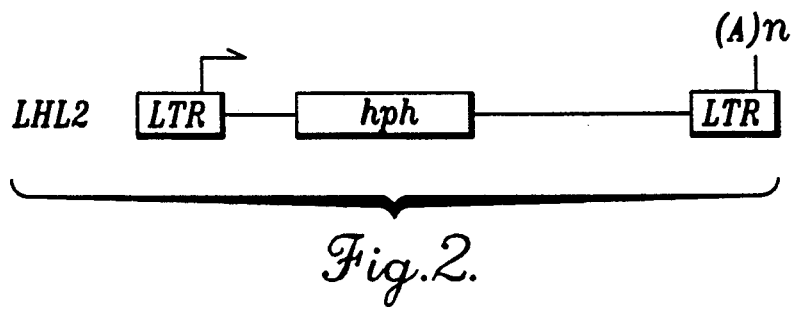
Figure 3:
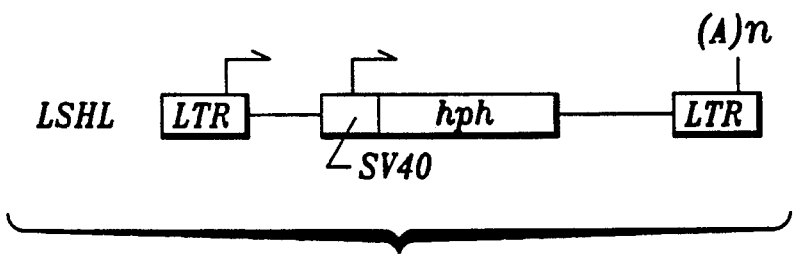
Figure 4:
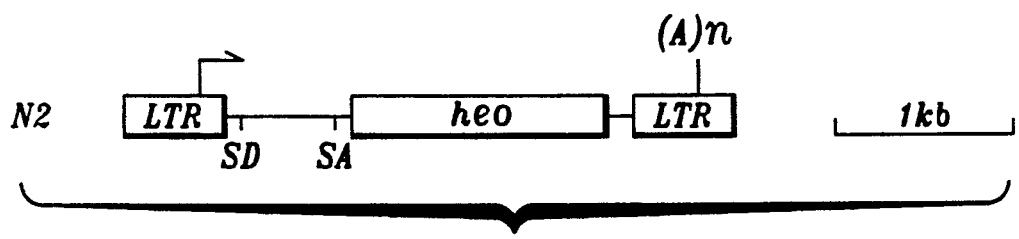

A process is provided for efficiently introducing genes into fibroblasts by using retroviral vectors, so as to permit and facilitate the expression of the introduced genes following implanation of the fibroblasts into a mammalian subject. As such, the invention provides a treatment for genetic disease by insertion of normal genes into skin fibroblasts of an affected individual. Current approaches to gene therapy have focused on the introduction of genes into pluripotent stem cells present in bone marrow. Retrovirus-mediated transfer and expression of genes introduced into hemopoietic progenitor cells of humans has been demonstrated. Nature 320: 275-277, 1986. However, recent reports suggest that transferred genes are poorly expressed in hemopoietic cells transplanted into animals. Proc. Natl. Acad. Sci. USA 83: 2566-2570, 1986. An explanation for the observed low and variable expression might involve suppression of gene expression during the extensive differentiation of transplanted hemopoietic cells. Fibroblasts provide an alternative target tissue for gene therapy. Skin fibroblasts are easily obtained and reintroduced and can be propagated for a short time in culture. Fibroblasts show little, if any, differentiation after transplantation, and so genes introduced into fibroblasts should not be subject to suppression as a result of alteration in gene-expression patterns during differentiation. The disclosed process provides infection and expression efficiencies of greater than fifty percent, which is surprisingly high, considering that normal human diploid fibroblasts were resistant to gene transfer by other methods. Furthermore, the growth characteristics of human fibroblasts, which are known to depend upon the age of the cell donor, do not affect the efficiency of gene transfer and expression using the subject method.

In the illustrative embodiments discussed below, retroviruses carrying selectable genes for neomycin or Hygromycin-B resistance conferred drug resistance to greater than 50% of the human fibroblasts after a single exposure to retrovirus-containing medium. Transfer was achieved in the absence of helper virus by using amphotropic retrovirus packaging cells. Thus, using the disclosed technique, skin fibroblasts can be considered suitable recipients for therapeutic genes to cure genetic disease. Toward this end, a replication-defective retrovirus vector containing a human adenosine deaminase (ADA) cDNA was used to infect ADA− fibroblasts from a patient with ADA deficiency. The infected cells produced twelve times more ADA enzyme than fibroblasts from normal individuals. Since the effects of ADA deficiency can be partially reversed by supplying the missing enzyme via red blood cell transfusions, the disclosed enzyme replacement therapy by retroviral gene transfer into autologous fibroblasts is considered to be a promising form of gene therapy.

Since both G418 and Hygromycin-B were shown to be effective selective agents for various human diploid fibroblast lines, the retroviral vectors shown in FIGS. 1 to 4 were constructed carrying one of two drug-resistance genes, the neomycin phosphotransferase gene (neo) or the hygromycin phosphotransferase gene (hph), which respectively confer resistance to G418 or Hygromycin-B. Two human diploid fibroblast cell lines were infected with these retroviral vectors to determine which configuration of sequences within the construct conferred drug resistance most efficiently, as measured by both the ability of limiting dilutions of virus to induce drug-resistant colony formation (virus titre) and the proportion of cells converted to drug resistance in one exposure to large amounts of virus (infection efficiency). As described below, using the high-titre N2 and LHL vectors (FIGS. 4 and 1), a majority and up to 87% of the infected cells became drug resistant (Table 2). For all of the vectors, the infection efficiencies were roughly proportional to titre. In both human diploid fibroblast lines, the infection efficiency for each vector reached a plateau at the same dilution of virus-containing medium. This suggests that the important factor for efficient infection of normal fibroblast cells is not the quantity of virus but rather other factors such as specific virus constructions.

The growth characteristics of human fibroblasts are known to depend on the age of the cell donor. To determine if these differences affect the efficiency of infection, four human diploid fibroblast lines from donors of different ages were infected with the two high-titre vectors N2 and LHL. The infection efficiency was similar for all of the human diploid fibroblast lines and was not related to donor age (Table 3).

To determine if a gene of therapeutic interest would be expressed well in normal fibroblasts, a vector for expression of adenosine deaminase (ADA) was constructed. ADA deficiency results in lethal severe combined immunodeficiency due to accumulation in plasma of adenosine and deoxyadenosine, which are considered to be selectively toxic to lymphocytes. If the patient's fibroblasts were genetically modified to express ADA, the normal metabolism of circulating adenosine and deoxyadenosine initiated by ADA might allow lymphocyte function to develop.

Figure 5:
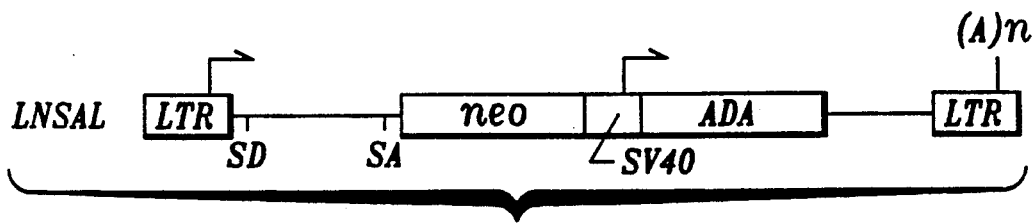

Referring to FIG. 5, the ADA vector LNSAL was made by inserting an ADA cDNA (Valerio, D., et al., Gene 31:147-153, 1984) linked to a SV40 early region enhancer/promoter downstream of the neo gene in N2. Helper-free virus was made by introduction of LNSAL into PA317 amphotropic retrovirus-packaging cells (ATCC No. CRL 9078), as described in Mol. Cell. Biol. 6:2895-2902, 1986, hereby incorporated by reference. LNSAL virus, at a titre of approximately $10^6$ G418-resistant cfu/ml when assayed on NIH 3T3 cells, was used to infect human diploid fibroblast skin cell line SF03, which was isolated from a patient with ADA deficiency. SF03 cells lack detectable ADA activity (less than 0.01 umol/hr/mg protein) and are killed by 2 mM adenosine, a concentration that has no effect on normal human diploid fibroblasts. Using either G418 or adenosine, the expression of either neo and the ADA gene was assayed in LNSAL-infected cells. The number of drug-resistant colonies formed in G418 or adenosine was essentially the same, about $10^5$ ml.

To confirm that the LNSAL-infected SF03 cells produced active ADA, random populations and clonal lines of G418- or adenosine-resistant cells were assayed for ADA activity. After infection, SF03 cells produced twelvefold more ADA than normal HDF (Table 4). No differences were seen in the ADA levels from cells selected in G418 or adenosine, indicating that both genes in LNSAL were expressed concurrently (Table 4). When isolated clones of G418-resistant cells were analyzed for ADA expression, as much as twenty-three times the ADA activity of normal fibroblasts was found (data not shown). These genetically modified fibroblasts produced relatively high levels of ADA in comparison with other human cell types as well (Table 4). Furthermore, the ADA produced from the transferred gene was shown to possess normal kinetic and structural properties and to bind to ADA-complexing protein present in ADA− fibroblasts. In summary, these results demonstrate faithful transfer and high-level expression of the ADA cDNA by the LNSAL retrovirus in normal human fibroblasts.

An estimate can be made of the number of genetically modified fibroblasts needed to effectively treat a human subject, based on the production of enzyme in infected fibroblasts and the amount of enzyme provided by existing therapies. For example, ADA-deficient patients can be treated by transfusion of one unit of red blood cells to provide a temporary source of the missing enzyme. Lancet ii: 743-746, 1975; Semin. hematol. 17: 30-43, 1980. ADA activity in red blood cells is 0.036 umol/hr/mg cell protein, and in the representative LNSAL-infected ADA$^-$ fibroblasts was about 12 umol/hr/mg of cell protein. Assuming 1 mg protein is present in $10^6$ fibroblasts or $4 \times 10^7$ red blood cells, then ADA activity produced by $4 \times 10^8$ fibroblasts is equivalent to one unit of red blood cells ($2 \times 10^{12}$ cells). Implantation of this number of genetically modified fibroblasts is feasible. Experiments in rats have shown that transplanted fibroblasts will persist for over 13 months. Transplantation 36: 552-557, 1984. Thus, when compared to the 20- to 30-day half-life of ADA in transfused red blood cells, continued production of ADA in fibroblasts might allow effective treatment with even smaller doses of genetically modified cells.

Procedures for introducing such genetically modified fibroblasts into a mammalian subject include subcutaneous injection of suspended cells, as generally described in Pediatr. Res. 16: 259-260, 1982, and Pediatr. Res. 16: 260-261, 1982, both of which are hereby incorporated by reference. Full thickness skin equivalent structures can also serve as the transplantation vehicle. For example, the genetically modified fibroblasts may be implanted in an artificial skin of cultured dermal and epidermal cells that can be quickly vascularized when transplanted onto freshly prepared graft beds, such as is described in Transplantation 36: 552-557, 1984, and Science 211: 1052-1054, 1981, both of which are hereby incorporated by reference. Alternatively, the genetically modified fibroblasts can be intraperitoneally or intravenously injected, leading to colonization of peritoneal serosa and omentum or pulmonary parenchyma, respectively. Of importance in deciding which route of implantation to use will be accessibility of the genetically modified fibroblasts to circulating plasma.

Given the relatively high infection efficiency of normal fibroblasts using retroviral vectors, up to 87 percent in these preliminary experiments, it is contemplated that batches of fibroblasts can be exposed to virus and then implanted without screening for a co-introduced selectable gene. This provides advantages because the diploid fibroblasts are relatively short-lived in cell culture. Furthermore, the retroviral vector need only carry the therapeutic gene, and not an additional selectable gene, and thus potential suppression of one gene by the other is avoided.

Given indications that implanted fibroblasts may be tolerated by nonautologous recipients, it is further contemplated that fibroblast banks can be established to supply genetically modified fibroblasts carrying preselected therapeutic genes to human patients at treatment centers remote from the supplier of the engineered cells. The therapeutic genes available in such fibroblast stocks may eventually encompass nonmammalian genes, such as bacterial sequences encoding for cholesterol-metabolizing enzymes.

The following Examples are presented to illustrate the advantages of the present invention and to assist one of ordinary skill in the making and using of the same. The Examples are not intended in any way to otherwise limit the scope of the disclosure or the protection granted by Letters Patent hereon.

EXAMPLE 1

Drug sensitivities of human diploid fibroblasts.

Three drugs were tested for their ability to kill human diploid fibroblasts (HDF): the neomycin analogue G418, Hygromycin-B (Hygro), and Methotrexate (Mtx). Four HDF lines were isolated from skin biopsies of normal human donors: HDF 78-18, from a 92-day female fetus; HDF 1-85, from newborn foreskin; HDF 79-81, from a 26-year old male; and HDF 72-46, from a 29-year old male. The four fibroblast lines were isolated using standard methods (Meth. Cell Biol. 219:255-276, 1980, hereby incorporated by reference) and were maintained in culture for 22 to 31 population doublings using Dulbecco-Vogt Modified Eagles Medium (D MEM) supplemented with 10% fetal bovine serum (FBS). NIH 3T3 immortalized mouse fibroblasts served as a control.

Cells were seeded at $10^4$ per 3.5-cm dish in D MEM plus 10% FBS and drug, except for Mtx selection where 10% dialyzed FBS was used. Drug-resistant cells were scored after 10 days. The results, in terms of the drug concentrations needed for complete cell killing, are shown in Table 1.

TABLE 1

| Drug Concentrations Needed For Complete Cell Killing | | | | | |
|---|---|---|---|---|---|
| Drug | Fetal HDF 78-18 | Newborn HDF 1-85 | Adult HDF 79-81 | Adult HDF 72-46 | Mouse NIH 3T3 |
| G418 (ug/ml) | 500 | 500 | 1000 | 500 | 1000 |
| Hygro (ug/ml) | 12 | 50 | 50 | 25 | 400 |
| Mtx (uM) | >1000 | >1000 | >10 | >1000 | 0.1 |

G418 and hygromycin-B concentrations are expressed as weight of dry powder with activities of 50% and 950 U/mg, respectively. With the exception of HDF 78-18, all of the human diploid fibroblast lines formed colonies at the highest concentration of Mtx used. HDF 78-18 did not form colonies, but viable cells (by the trypan blue exclusion test) remained after 15 days of selection.

As shown in Table 1, the drug sensitivities of normal human diploid fibroblasts were found to be significantly different from the immortalized fibroblasts. For example, human diploid fibroblast cell lines were resistant to killing by $10^{-5}$M Methotrexate, and most were resistant to more than $10^{-3}$M Methotrexate, whereas the NIH 3T3 cells were efficiently killed by $10^{-7}$M Methotrexate. The HDF cell lines were about tenfold more sensitive to killing by Hygromycin-B than the control cells, and cell death occurred quickly. Only the neomycin analogue G418 showed similar toxicity for both the human and mouse cells. These results show that G418 or hygromycin, but not methotrexate, are suitable selective agents for gene transfer into human diploid fibroblasts.

EXAMPLE 2

Gene transfer into human diploid fibroblasts.

Since both G418 and Hygromycin-B were effective selective agents for the human diploid fibroblast lines, vectors were constructed carrying one of two drug-resistance genes, the neomycin phosphotransferase gene (neo) or the hygromycin phosphotransferase gene (hph), which respectively confer resistance to G418 or Hygromycin-B. Two human diploid fibroblast cell lines were infected with these retroviral vectors to determine which configuration of sequences within the vector conferred drug resistance most efficiently, as measured by both the proportion of cells converted to drug resistance in one exposure to large amounts of virus (infection efficiency) and the ability of limiting dilutions of virus to induce drug-resistant colony formation (virus titre).

Representative retroviral vectors are shown in FIGS. 1 to 5. Each of these vectors contained one of the selectable genes inserted between long terminal repeats (LTRs) and viral replication signals from Moloney murine leukemia virus (Mo-MLV), except the LSHL and LHL2 vectors which had Moloney murine sarcoma virus sequences on the left (5') side and Mo-MLV on the right. Arrows indicate promoters; SV40 indicates the early region enhancers and promoter of SV40 virus; $(A)_n$ indicates polyadenylation signals; and SD and SA are splice donors and splice acceptors, respectively. The normal splice donor in Mo-MLV was removed by a single base substitution in LHL2 and LSHL. The N2 (Science 222:385–389, 1983) and LNSAL vectors contain the gene coding for neomycin phosphotransferase (neo) (J. Molec. Biol. 150:1–14, 1981). Vectors LHL, LHL2, and LSHL contain the hygromycin phosphotransferase gene (hph) from pLG90 (Gene 25:179–188, 1983). N2, LHL, and LNSAL contain approximately 400 base pairs of the gag encoding region of Mo-MLV, while LHL2 and LSHL do not contain this region.

Several strategies have been used for the generation of helper virus-free retrovirus vectors. Cell lines producing amphotropic helper-free viral vectors were generated as described in Somatic Cell Molec. Genet. 12:175–183, 1986. One strategy involves transfection of a retrovirus vector carrying a dominant selectable marker into a retrovirus packaging cell line, followed by selection for cells containing the vector. In this way, the vectors N2, LHL, and LNSAL were produced in the packaging cell line PA317 (ATCC No. CRL 9078), whereas vectors LHL2 and LSHL were produced by using PA12 cells (Molec. Cell. Biol. 5:431–437, 1985). No helper virus (less than 1 per ml) was produced from these clones, as measured by the sensitive S+L- assay (Molec. Cell. Biol. 5:431–437, 1985). A second strategy for production of helper-free virus involves transfection of the retrovirus packaging construct DNA into cells infected with the viral vector (Miller et al., Mol. Cell. Biol. 5:431–437, 1984). Helper-free virus produced in this way will be more homogeneous than that produced following transfection of the vector DNA. However, this strategy is time-consuming, as one must first isolate vector-infected cells, introduce the retrovirus packaging construct DNA into the cells by cotransfection with a selectable marker, and then isolate and screen transfected clones for production of helper-free virus vector.

The fibroblast cells to be infected were seeded at $5 \times 10^5$ per 60-mm petri dish and incubated overnight in standard growth medium. The medium was then replaced with 4 ml medium containing 4 ug/ml Polybrene (Sigma), and various amounts of medium that had been exposed to the virus-producing cells were added. After 16 hours, the infected cells were suspended by use of trypsin. The NIH 3T3 cells were diluted 1:10 into selective media and plated onto 60-mm dishes, while the HDF lines were divided 1:10 and 1:100 into 100-mm dishes containing selective media to prevent overlap of the loosely organized colonies of migrating HDF. Resistant colonies were scored after 10–12 days. The results are shown in Table 2.

TABLE 2

| | Titer and Infection Efficiencies of Four Vectors on Two HDF Lines | | | | |
|---|---|---|---|---|---|
| | Fetal HDF 78-18 | | Adult HDF 79-81 | | Mouse NIH 3T3 |
| Vector | Virus Titre (cfu/ml) | Infection Efficiency (%) | Virus Titre (cfu/ml) | Infection Efficiency (%) | Virus Titre (cfu/ml) |
| N2 | $1.1 \times 10^6$ | 87 | $8.8 \times 10^5$ | 73 | $3.2 \times 10^7$ |
| LHL | $1.6 \times 10^6$ | 55 | $2.1 \times 10^6$ | 52 | $2.4 \times 10^6$ |
| LSHL | $4.6 \times 10^5$ | 17 | $4.2 \times 10^5$ | 19 | $1.0 \times 10^6$ |
| LHL2 | $2.0 \times 10^3$ | <1 | $1.4 \times 10^3$ | <1 | $1.0 \times 10^4$ |

Titres listed are corrected for plating efficiency by dividing the observed viral titer by the plating efficiency. Plating efficiency equals the number of colonies growing without selection divided by the number of viable cells plated and was 0.09, 0.08, and approximately 1.00 for HDF 78-18, HDF 79-81, and NIH 3T3 cells, respectively. Exposure to virus had no effect on plating efficiency. Infection efficiency for an infected cell population was measured by seeding equal numbers of cells into selective or nonselective medium and dividing the number of drug-resistant colonies by the number of colonies growing in the absence of selection.

As shown in Table 2, the highest efficiency of gene transfer occurred using the N2 and LHL vectors: a majority of up to 87% of the infected human diploid fibroblast cells became drug resistant. For all of the vectors, the infection efficiencies were roughly proportional to titre. Furthermore, in the HDF lines, the infection efficiency for each vector reached a plateau at the same dilution of virus-containing medium (1:10 dilution of medium exposed to virus-producing cells; data not shown). These results suggest that the important factor for efficient infection of human diploid fibroblast cells is the quality and not the quantity of the virus.

EXAMPLE 3

Effect of donor age human diploid fibroblast infection.

The growth characteristics of human fibroblasts are known to depend on the age of the cell donor. Exp. Cell Res. 37:614–636, 1963. To determine if these differences affect the efficiency of retroviral infection, four human diploid fibroblast lines from donors of different ages were infected with the two high-titre vectors N2 and LHL.

N2 or LHL virus was used to infect the four HDF lines as described above. The infection efficiencies and titres were determined as described for Table 2. The results are shown in Table 3, in which values from two experiments (a and b) are ordered by row. Plating efficiencies (cell line, expt. a, expt. b) were: 78-18, 0.09, 0.09; 1-85, 0.23, 0.42; 79-81, 0.08, 0.03; and 72-46, nd, 0.03.

TABLE 3

The Effects of Donor Age on Virus Titre and Infection Efficiency

| Vector | Fetal HDF 78-18 Virus Titre (cfu/ml) | Fetal HDF 78-18 Inf. Eff. (%) | Newborn HDF 1-85 Virus Titre (cfu/ml) | Newborn HDF 1-85 Inf. Eff. (%) | Adult HDF 79-81 Virus Titre (cfu/ml) | Adult HDF 79-81 Inf. Eff. (%) | Adult HDF 72-46 Virus Titre (cfu/ml) | Adult HDF 72-46 Inf. Eff. (%) |
|---|---|---|---|---|---|---|---|---|
| N2 a | $1.1 \times 10^6$ | 87 | $8.9 \times 10^5$ | 74 | $8.8 \times 10^5$ | 73 | nd* | nd |
| b | $1.7 \times 10^6$ | 31 | $3.1 \times 10^6$ | 48 | $4.1 \times 10^6$ | 35 | $7.3 \times 10^6$ | 50 |
| LHL a | $1.1 \times 10^6$ | 55 | $6.0 \times 10^5$ | 46 | $2.1 \times 10^6$ | 52 | nd | nd |
| b | $1.7 \times 10^5$ | 33 | $4.5 \times 10^5$ | 41 | $1.5 \times 10^6$ | 19 | $1.2 \times 10^6$ | 24 |

*nd = not determined.

As shown in Table 3, the infection efficiencies were similar for all of the human diploid fibroblast lines, indicating that the efficiency of retroviral infection is not related to donor age.

EXAMPLE 4

Expression of an introduced therapeutic gene in human diploid fibroblasts.

To determine if a gene with therapeutic importance could be introduced into and expressed well in normal fibroblasts, a retroviral vector for expression of adenosine deaminase (ADA) was constructed.

The ADA$^-$ HDF line SF03 was infected with the LNSAL virus (FIG. 5) and selected in either 1 mg/ml G418 or 2 mM adenosine in 10% horse serum and 1 mM uridine. Drug-resistant clones were pooled and assayed for ADA activity as described in Biochem. J. 133:117-123, 1973. The experimental results are shown in Table 4, in which ADA activities in other normal human cell types are also listed for comparison. Purine nucleoside phosphorylase (PNP) activity was measured as an internal control. Activities are um ol/hr/mg total protein. Values are mean ±SD ($n \geq 4$).

TABLE 4

ADA Activity in Normal Human Cells and Infected ADA$^-$ HDF

| Enzyme | Normal HDF | ADA$^-$ HDF | Peripheral Blood T Cells | Red Blood Cells | LNSAL ADA$^-$ HDF G418 | LNSAL ADA$^-$ HDF adenosine |
|---|---|---|---|---|---|---|
| ADA | 0.9 ± 0.4 | 0.01 | 7.6 ± 1.4 | 0.04 ± 0.01 | 12 ± 6 | 11 ± 3 |
| PNP | 0.7 ± 0.3 | 0.7 ± 0.1 | 2.3 ± 0.3 | 1.6 ± 0.2 | 1.0 ± 0.5 | 0.9 ± 0.3 |

As shown in Table 4, after infection, the SF03 cells produced twelvefold more ADA than normal HDF. Essentially no differences were observed in the ADA levels from cells selected in G418 or adenosine, indicating that both genes in the introduced LNSAL vector were expressed concurrently. This result is in contrast to results obtained with other vectors carrying two genes, where selection for one of the genes results in suppression of expression of the other gene. Cell 39:459-467, 1984. These genetically modified fibroblasts produced relatively high levels of ADA in comparison with other human cell types as well.

The Michaelis constant ($K_m$) and electrophoretic pattern of the ADA from the infected SF03 cells were determined as described in Palmer, T. D., et al., Proc. Natl. Acad. Sci. USA 84:1055-1059, 1987, hereby incorporated by reference. The $K_m$ measured with adenosine as substrate was 26.2±1.9 uM, which is the same as the normal value of 29.2±2.5 uM (Biochem. J. 133:117-123, 1973). The starch gel-electrophoretic pattern (not shown) was typical of normal skin fibroblasts and showed the ADA 1 red blood cell phenotype and fibroblast tissue-specific ADA isozyme. Mixed homogenates of normal red blood cell ADA and ADA$^-$ skin fibroblasts also generate the tissue-specific ADA isozyme. Proc. Natl. Acad. Sci. USA 75:3876-3880, 1978. Hence, the ADA produced from the transferred gene possessed normal kinetic and structural properties and can bind to ADA complexing protein present in ADA$^-$ fibroblasts. Analysis of genomic DNA from LNSAL virus-producing cells and LNSAL-infected SF03 fibroblasts, by Southern blotting after cleavage with restriction enzymes that cleave once in each viral LTR, revealed that the integrated LNSAL virus in all samples was identical to the original LNSAL plasmid (not shown). In summary, these results demonstrate faithful transfer and high-level expression of ADA by the LNSAL retrovirus in human diploid fibroblast. It is contemplated that upon implantation, these genetically modified ADA$^+$ skin fibroblasts can rapidly metabolize exogenous deoxyadenosine and adenosine and convert these toxic compounds primarily into hypoxanthine, which would not be toxic to ADA-deficient patients.

While the present invention has been described in conjunction with preferred embodiments, one of ordinary skill after reading the foregoing specification will be able to effect various changes, substitutions of equivalents, and alterations to the subject matter set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A process of gene transfer into diploid fibroblasts in vitro, comprising the step of:
   genetically modifying diploid fibroblasts explanted from a mammalian subject by a process consisting essentially of introducing into said fibroblasts a retroviral construct comprising a first nucleotide sequence encoding a first expression product, a viral long terminal repeat and a promoter sequence upstream of said first nucleotide sequence, and a viral long terminal repeat and a polyadenylation sequence downstream of said first nucleotide sequence, wherein said retroviral construct lacks one or more of the gag, pol, and env sequences required for retroviral replication, by contacting said fibroblasts with said retroviral construct in a virus-containing medium having a viral titer of at least about $10^5$ cfu/ml on NIH 3T3 fibroblasts to produce a population of fibroblasts at least 1% of which express said first expression product.

2. The process of claim 1, wherein said retroviral construct further comprises a second nucleotide sequence encoding a second expression product, and wherein one of the first and the second expression products confers resistance to a selectable marker substance.

3. The process of claim 2, wherein said selectable marker substance is selected from the group consisting of G418 and Hygromycin-B.

4. The process of claim 1, wherein said diploid fibroblasts are explanted from the tissue of a mammalian subject.

5. The process of claim 1, wherein said mammalian subject is a human.

6. The process of claim 2, wherein the other of the first and the second expression products is selected from the group consisting of enzymes, hormones, and precursors thereof.

7. The process of claim 6, wherein the other of the first and the second expression products is selected from the group consisting of adenosine deaminase, purine nucleoside phosphorylase, and blood clotting factors.

* * * * *